United States Patent
Brumbaugh et al.

(10) Patent No.: US 8,057,830 B2
(45) Date of Patent: Nov. 15, 2011

(54) CLEANSING COMPOSITIONS AND METHODS OF REDUCING SKIN IRRITATION

(75) Inventors: Ernest H. Brumbaugh, Rockford, MI (US); Douglas K. Feenstra, Wyoming, MI (US)

(73) Assignee: Access Business Group International LLC, Ada, MI (US)

( * ) Notice: Subject to any disclaimer, the term of this patent is extended or adjusted under 35 U.S.C. 154(b) by 774 days.

(21) Appl. No.: 11/385,953

(22) Filed: Mar. 21, 2006

(65) Prior Publication Data

US 2007/0224155 A1    Sep. 27, 2007

(51) Int. Cl.
*A61K 36/00* (2006.01)
*A61K 36/53* (2006.01)
*A61K 36/886* (2006.01)

(52) U.S. Cl. .................................. 424/744; 424/725
(58) Field of Classification Search .................. 424/725, 424/744
See application file for complete search history.

(56) References Cited

U.S. PATENT DOCUMENTS

| | | | | |
|---|---|---|---|---|
| 5,266,318 | A * | 11/1993 | Taylor-McCord | 424/744 |
| 6,271,001 | B1 | 8/2001 | Clarke et al. | |
| 6,350,594 | B1 | 2/2002 | Clarke et al. | |
| 2004/0126430 | A1 * | 7/2004 | Angel et al. | 424/487 |
| 2004/0175439 | A1 | 9/2004 | Cyr | |
| 2004/0213864 | A1 | 10/2004 | Slimak | |
| 2006/0110415 | A1 | 5/2006 | Gupta | |
| 2007/0224154 | A1 * | 9/2007 | Brumbaugh et al. | 424/74 |
| 2007/0269534 | A1 * | 11/2007 | Ramirez et al. | 424/677 |
| 2007/0292459 | A1 * | 12/2007 | Cooper et al. | 424/401 |

FOREIGN PATENT DOCUMENTS

JP      2001-172159 A  *  6/2001
WO   WO 2006/079109 A2    7/2006

OTHER PUBLICATIONS

Ito, M., "Studies on perilla, agarwood, and cinnamon through a combination of fieldwork and laboratory work," *J. Nat.-Med.*, 2008, 62, pp. 387-395.*

* cited by examiner

*Primary Examiner* — James H. Alstrum-Acevedo
(74) *Attorney, Agent, or Firm* — Brinks Hofer Gilson & Lione; G. Peter Nichols

(57) ABSTRACT

Cleansing compositions are described that comprise at least one surfactant, at least one extract of a Lamiaceae family plant, and at least one extract of a Liliaceae family plant. The at least one extract of the Lamiaceae family plant and the at least one extract of the Liliaceae family plant are present in effective amounts to at least partially counteract skin irritation induced by the at least one surfactant. Methods of reducing skin irritation induced by a surfactant comprise contacting skin with a detergent comprising at least one surfactant, at least one extract of a Lamiaceae family plant, and at least one extract of a Liliaceae family plant, wherein the at least one extract of the Lamiaceae family plant, and the at least one extract of the Liliaceae family plant at least partially counteract irritation induced by the at least one surfactant.

13 Claims, No Drawings

CLEANSING COMPOSITIONS AND METHODS OF REDUCING SKIN IRRITATION

TECHNICAL FIELD

The present teachings relate to compositions and methods for reducing skin irritation induced by a surfactant.

INTRODUCTION

Skin irritation induced by surfactant-containing compositions—particularly cleansing compositions and other household products that may come in contact with a consumer's skin during use (e.g., hand dishwashing detergents, soaps, shampoos, and the like)—is a highly undesirable drawback to the use of such products. Many surfactants commonly added to detergents are particularly irritating to the skin. Examples of such commonly used surfactants include linear alkylbenzene sulfonate (LAS), sodium lauryl sulfate (SLS), and sodium lauryl ether sulfate (SLES).

Conventional attempts to impart mildness to products such as hand dishwashing detergents have involved careful selection of the surfactants employed, the use of occlusive film-formers to block detergent molecules from contacting the skin, and reducing the critical micelle concentration of detergent in order to decrease the amount of potentially irritating free surfactant molecules present in a wash solution. These methods attempt to alter the severity of a surfactant system towards skin (e.g., by blocking contact with the skin or limiting exposure of surfactant monomers to the skin).

In other approaches, milder co-additive surfactants, such as betaines, have been employed to help mitigate the irritancy of harsher surfactants that may be present, such as SLES and LAS surfactants. More recently, protease enzymes have been added to hand dishwashing detergents to promote skin exfoliation and skin cell renewal. However, the addition of enzyme does not alter the harshness of the surfactant system. Moreover, since the action of the enzyme removes skin tissue, this process must be carefully controlled.

All of the above-described strategies for reducing skin irritation are directed at macroscale solutions to the problem, and do not attempt to solve the problem at the more fundamental molecular level.

SUMMARY

The scope of the present invention is defined solely by the appended claims, and is not affected to any degree by the statements within this summary.

A cleansing composition embodying features of the present invention comprises: at least one surfactant; at least one extract of a Lamiaceae family plant; and at least one extract of a Liliaceae family plant. The at least one extract of the Lamiaceae family plant and the at least one extract of the Liliaceae family plant are present in effective amounts to at least partially counteract skin irritation induced by the at least one surfactant.

A method of reducing skin irritation induced by a surfactant embodying features of the present invention comprises contacting skin with a detergent comprising at least one surfactant, at least one extract of a Lamiaceae family plant, and at least one extract of a Liliaceae family plant. The at least one extract of the Lamiaceae family plant and the at least one extract of the Liliaceae family plant at least partially counteract irritation induced by the at least one surfactant.

DETAILED DESCRIPTION

Surfactant-containing compositions and methods for reducing skin irritation induced by a surfactant have been discovered and are described hereinbelow, which relieve and/or prevent skin irritation by initiating a biological response in an individual. By way of introduction, it has been discovered that the irritation potential of surfactant systems may be decreased by reducing the inflammation response of human skin to these same surfactant systems; thus, by reducing the inflammation response, the surfactant formulations will be milder to the skin. As further described below, it has been discovered that this inflammation response may be reduced by incorporating into a surfactant-containing composition various botanical extracts that serve to counteract the irritating effects of the surfactants.

A series of bioassays and screenings of various response mechanisms resulted in the selection of IL-1 alpha, a protein indicative of inflammation, as a reliable and applicable target response. IL-1 alpha is one cytokine often released near the beginning of the inflammation cascade, which ultimately leads to a human biological response resulting in visible and/or perceptual signs of irritation. Accordingly, by reducing the initial response to an irritant, such as a surfactant, the ultimate damaging reaction can be reduced, prevented, and/or eliminated.

The procedure for conducting IL-1 alpha assays is as follows: Co-cultures of fibroblasts and keratinocytes, the primary cell types found in skin, are established using 100,000 fibroblasts and 200,000 keratinocytes per well. These types of cells are those found in the outer layers of the skin exposed to detergent during every day use. An irritant, for example the surfactant package used in a dish detergent (Example 1 below), is then applied to the coculture wells to initiate the production and secretion of pro-inflammatory cytokines by the cells. One such cytokine is human interleukin-1 alpha or IL-1$\alpha$. In the body, this protein is a key mediator of the host response to infections and various inflammatory challenges. Once produced, IL-1$\alpha$ stimulates production of other pro-inflammatory cytokines and bioactive molecules. Together, these biological molecules send the message that something is wrong and the keratinocytes and fibroblasts need help. This is called the inflammatory response.

The amount of secreted IL-1$\alpha$ is directly related to the intensity of the inflammatory response. In vitro, the concentration of IL-1$\alpha$ secreted by the co-culture cells in response to the irritant can be measured via a precise laboratory technique known as an Enzyme Linked Immuno-Sorbent Assay or ELISA. Thus, to test botanical materials for mildness, a lessening of IL-1$\alpha$ secretion, the mildness agents were added with the chemical irritant. When a reduction in IL-1$\alpha$ expression was observed, the mildness agents were successful. Theoretically, there are several mechanisms by which this could have been achieved at the cellular level. Without wishing to be bound to a particular theory or in any way limit the scope of the appended claims or their equivalents, it is presently believed that these mechanisms may include one or more of the following: the mildness agent could block the transcription of the DNA to RNA, translation of the RNA to protein, and/or release of the IL-1$\alpha$ from the cells. In addition, the mildness agents might bind to the irritant rendering it less effective and/or they might block receptor sites on the cell. The mildness agent may also have stopped the cascade after the irritant works on the cell. Whatever the mechanism, the net result is the same. There is less IL-1$\alpha$ released by the cells which correlates to inhibition of events in the inflammatory cascade and ultimately, less inflammation.

Heretofore, the efficacy of certain botanicals for reducing, preventing or eliminating surfactant-induced skin irritation has not been recognized in the industry. On the contrary, any botanicals present in detergents were present in low concentrations, and limited in use primarily to "leave on" (as opposed to "wash off") products where long-term effects might be possible. Indeed, the use of certain botanical extracts described herein capable of at least partially counteracting irritation induced by a surfactant (e.g., by initiating a biological response in the skin) has not been previously known.

Throughout this description and in the appended claims, the following definitions are to be understood:

The phrase "skin irritation" refers to any undesirable effect produced in or on the surface of skin, including but not limited to pain, sensitivity, chafing, abrasion, inflammation, swelling, redness or other discoloration, dryness, bleeding or the like, and combinations thereof.

The phrase "botanical extract" refers to any material or combination of materials produced by and/or obtained from a plant as well as chemically related derivatives thereof. It is to be understood that this phrase includes any synthetically prepared analogues of a natural material. In addition, as used herein, this phrase is to be understood as including silicone derivatives of natural and/or nature-identical substances, including but not limited to the silicone-containing materials dimethiconol panthenol and dimethylsilanediol hyaluronate.

In some embodiments, a method of reducing skin irritation induced by a surfactant comprises contacting skin with a detergent comprising at least one surfactant and at least one botanical extract, wherein the at least one botanical extract at least partially counteracts irritation induced by the at least one surfactant.

In some embodiments, the at least one botanical extract initiates a biological response in the skin, which in some embodiments corresponds to the reduction, prevention, and/or elimination of an inflammation response in the skin. In some embodiments, the at least one botanical extract reduces, prevents or eliminates IL-1 alpha secretion.

Table 1 shows representative botanical extracts (and their representative suppliers) that can be used in accordance with the present invention, as well as data for the corresponding percent reductions in IL-1 alpha secretion that were observed for a hand dishwashing detergent at botanical concentrations of 1%, 0.1%, and 0.1% by weight. These were prepared using a serial dilution technique: 1.0 g botanical was mixed well with 99.0 g dish detergent to give the 1.0% formulation; next, 10.0 g of the 1.0% solution was mixed well with 90.0 g of the dish detergent to give the 0.1% formulation; finally, 10.0 g of the 0.1% solution was mixed well with 90.0 g of the dish detergent to give the 0.01% formulation.

In some embodiments, as shown in Table 1, the presence of certain botanical extracts in the dish detergent system reduced IL-1 alpha secretion by up to about 30%, and in some instances more.

TABLE 1

Representative Botanical Extracts and IL-1 α Reduction Data

| Botanical Extract | Percent IL-1 α Reduction | | | AVG | Supplier | Source |
|---|---|---|---|---|---|---|
| | 1% | 0.1% | 0.01% | | | |
| Shiso Extract | 17.3 | 45.9 | 51.2 | 38.13 | Barnet | *Perilla Ocymoides* Ext |
| Rosmarinic Acid | 20.1 | 31.8 | 34.5 | 28.80 | Cayman | |
| Epicatechin | 41.6 | 22.1 | 26.2 | 29.97 | Aldrich | *Camellia Sinensis* |
| Green Tea Extract | 31.1 | 22.9 | 30.1 | 28.03 | Symrise | *Camellia Sinensis* |
| Catechin | 7.90 | 24.90 | 19.50 | 17.43 | Aldrich | *Camellia Sinensis* |
| WHITE TEA COMPLEX | 6.30 | 18.30 | 16.10 | 13.57 | Barnet | *Camellia Sinensis* |
| EGCG | 6.90 | 12.10 | 12.50 | 10.50 | Aldrich | *Camellia Sinensis* |
| Rosehip Extract | 49.9 | 29.6 | 9.4 | 29.63 | Plantextrakt | Rose Hips |
| DERMALIGHT | 5.4 | 28.8 | 36.5 | 23.57 | SiLab | Nastursium Ext |
| Ginko Biloba | 14.20 | 26.50 | 25.80 | 22.17 | Floraceutical | |
| Jujube Extract | 12.60 | 24.60 | 17.30 | 18.17 | Draco | Jujube Seed Ext |
| DRAGODERM | 22.30 | 23.90 | 4.20 | 16.80 | Symrise | Wheat Protein |
| STRUCTURINE | 19.90 | 20.00 | 9.80 | 16.57 | SiLab | Hydrolyzed Lupin Protein |
| Himalyan Raspberry Extract | 17.40 | 11.70 | 20.10 | 16.40 | Barnet | *Rubus ellipticus* |
| Oat Extract | 12.00 | 11.00 | 22.00 | 15.00 | Symrise | |
| NET-STG | 13.20 | 11.40 | 14.70 | 13.10 | Barnet | Licorice Roots |
| DEFENSINE | 1.20 | 12.10 | 20.30 | 11.20 | SiLab | Wheat Germ Ext |
| COHESINE | 11.70 | 7.20 | 6.30 | 8.40 | SiLab | Hydrolyzed Sesame Ext |
| Willowherb Extract | 17.40 | 6.10 | 1.20 | 8.23 | Symrise | |
| Grapeseed Extract | -5.90 | 11.40 | 13.60 | 6.37 | Floraceutical | |
| SENSILINE | 2.40 | 3.80 | 6.70 | 4.30 | SiLab | Hydrolyzed Linseed Ext |
| TRIPLE A COMPLEX | 8.50 | -5.20 | 6.40 | 3.23 | Barnet | Algae + Mugwort Ext |
| Vitamin E acetate | 26.90 | 27.50 | 25.80 | 26.73 | Hoffman-LaRoche, Inc. | |
| VC-PMG | 12.30 | 23.80 | 29.70 | 21.93 | Barnet | Magnesium Ascorbyl Phosphate |
| D.S.H. C N | 19.24 | 16.43 | 22.25 | 19.31 | Exsymol | Dimethiconol Panthenol |
| Vitamin B12 | 13.00 | -3.20 | 17.70 | 9.17 | Roche Vitamins | |
| Vitamin C | 3.20 | 8.50 | 10.30 | 7.33 | BASF | |
| PHOSPHOLIPID PTC | 9.50 | 18.40 | 11.40 | 13.10 | Uniquema | Phospholipid |
| Ceramide | 9.10 | 14.70 | -0.60 | 7.73 | Takasago | |
| GLISTIN | 17.60 | 31.80 | 18.50 | 22.63 | Exsymol | glutaurylamidoethyl indole |
| Farnesol | 27.30 | 15.50 | 14.50 | 19.10 | Symrise | |
| LECINOL S-10 | 12.90 | 23.60 | 12.20 | 16.23 | Barnet | Hydrogentated Soy Lecithin |
| PHYTIC ACID EXTREME | 14.91 | 12.56 | 15.01 | 14.16 | Biosil | |
| D.S.B.C. | 16.74 | 13.07 | 7.46 | 12.42 | Exsymol | silanediol salicylate |

TABLE 1-continued

Representative Botanical Extracts and IL-1 α Reduction Data

| Botanical Extract | Percent IL-1 α Reduction | | | | Supplier | Source |
| --- | --- | --- | --- | --- | --- | --- |
| | 1% | 0.1% | 0.01% | AVG | | |
| AMINO DL-30 | 7.22 | 7.18 | 21.81 | 12.07 | Biosil | Dimethylsilanol Hyaluronate |
| Alpha bisabolol | −1.00 | 2.00 | 19.00 | 6.67 | Symrise | Chamomile |
| Vegebios of Sage | 6.54 | 9.73 | 17.15 | 11.14 | Barnet | Sage |
| Vegebios of Rosemary | 15.81 | 14.29 | 19.36 | 16.49 | Barnet | Rosemary |

By way of illustration, representative botanical extracts for use in accordance with the present invention include but are not limited to the following: extracts of plants in the Lamiaceae family; rosmarinic acid; extracts of *Camellia Sinensis*, rosehip extracts; nasturtium extracts; ginko biloba; jujube seed extract; wheat protein; hydrolyzed lupin protein; extracts of *Rubus ellipticus*; oat extract; licorice extract; wheat germ extract; hydrolyzed sesame extract; willowherb extract; grapeseed extract; hydrolyzed linseed extract; algae and mugwort extract; vitamin E; magnesium ascorbyl phosphate; dimethiconol panthenol; vitamin B12; vitamin C; phospholipids; ceramide lipids; glutaurylamidoethyl indole; farnesol; hydrogenated soy lecithin; phytic acid; silanediol salicylate; dimethylsilanol hyaluronate; alpha bisabolol; sage extracts; rosemary extracts; extracts of plants in the Liliaceae family; rosemary extracts; sage extracts; and the like; and combinations thereof.

In some embodiments, extracts of plants in the Lamiaceae family that can be used include but are not limited to extracts of *Perilla Ocymoides*, including but are not limited to shiso extracts, such as the extract of *Perilla Ocymoides* sold under the product name SHISO EXTRACT 100 by Barnet Products Corporation (Englewood Cliffs, N.J.).

In some embodiments, rosmarinic acid that can be used is derived from one or more of *Lavandula angustifolia* (Lamiaceae, lavender), *Melissa officinalis* (Lamiaceae, balm), *Mentha spicata* (Lamiaceae, spearmint), *Mentha×piperita* (Lamiaceae, peppermint), *Orthosiphon aristatus* (Lamiaceae, java yea), *Primula veris* (Primulaceae, cowslip flower), *Pilmonaria officinalis* (Boraginaceae, lungwort), *Rosemarinus officinalis* (Lamiaceae, rosemary), *Salvia officinalis* (lamiaceae, sage), *Salvia tribola* (Lamiaceae, sage), *Thymus serpyllum* (Lamiaceae, thyme), *Sanicula europaea* (Apiaceae, European *sanicle*), *Perilla* sp. (Lamiaceae, shiso), and the like, and combinations thereof.

In some embodiments, extracts of *Camellia Sinensis* that can be used include but are not limited to green tea extract, white tea extract, individual components of green tea extract and/or white tea extract (including but not limited to epicatechin, catechin, epigallocatechin gallate or EGCG, and the like), and any combination of the above. In some embodiments, the white tea extract is the extract sold under the product name WHITE TEA COMPLEX by Barnet Products Corporation.

In some embodiments, rosehip extract that can be used includes but is not limited to an extract containing dehydroascorbic acid (Vitamin C derivatives) prepared from approximately 2.0 g of rosehip powdered material which was extracted with 20 ml of a water and ethanol mixture (70:30 water/ethanol). This mixture was sonicated for a period of 10 minutes, and the resulting solution contained a 100 mg/ml rosehip extract used for various bioassays.

In some embodiments, a nasturtium extract that can be used includes but is not limited to the extract of Indian Cress flower sold under the product name DERMALIGHT by Silab (Cedex, France).

In some embodiments, jujube seed extract that can be used includes but is not limited to an extract containing jujobosides prepared from approximately 2.0 g of jujube seed powdered material which was extracted with 20 ml of a water and ethanol mixture (70:30 water/ethanol). This mixture was sonicated for a period of 10 minutes, and the resulting solution contained a 100 mg/ml jujube extract used for various bioassays.

In some embodiments, wheat protein that can be used includes but is not limited to non-hydrolyzed wheat protein, including but not limited to the endosperm of wheat grain sold under the product name DRAGODERM by Symrise Inc. (Teterboro, N.J.).

In some embodiments, hydrolyzed lupin protein that can be used includes but is not limited to the extract of sweet white lupin sold under the product name STRUCTURINE by Silab.

In some embodiments, an extract of *Rubus ellipticus* that can be used includes but is not limited to Himalayan raspberry extract, including but not limited to that sold under the product name HIMALAYAN RASPBERRY ROOT BG by Barnet Products Corporation.

In some embodiments, oat extract that can be used includes but is not limited to the avenanthramide-containing oat extract sold under the product name DRAGO-OAT-ACTIVE by Dragoco Inc. (Totowa, N.J.).

In some embodiments, licorice extract that can be used includes but is not limited to glycyrrhiza, glycerrhetic acid, glycyrrhizic acid, derivatives thereof (e.g., dipotassium glycyrrhizinate, stearyl glycyrrhetinate, and the like), and combinations of the above. In some embodiments, the dipotassium glycyrrhizinate is that sold under the product name NET-DG by Barnet Products Corporation. In some embodiments, the stearyl glycyrrhetinate is that sold under the product name NET-STG by Barnet Products Corporation.

In some embodiments, wheat germ extract that can be used includes but is not limited to the enzymatic system with glutathione auto-regeneration ability sold under the product name DEFENSINE BY Silab.

In some embodiments, hydrolyzed sesame extract that can be used includes but is not limited to that sold under the product name COHESINE by Silab.

In some embodiments, hydrolyzed linseed extract that can be used includes but is not limited to the combination of acid polysaccharides and peptidoglycans of linseed sold under the product name SENSILINE by Silab.

In some embodiments, the algae and mugwort extract that can be used includes but is not limited to that sold under the product name TRIPLE A COMPLEX by Barnet Products Corporation.

In some embodiments, the magnesium ascorbyl phosphate that can be used includes but is not limited to that sold under the product name NIKKOL VC-PMG by Barnet Products Corporation.

In some embodiments, the dimethylsilanediol hyaluronate that can be used includes but is not limited to that sold under the product name D.S.H. CN by Exsymol S.A.M. (Monaco).

In some embodiments, the phospholipids that can be used include but are not limited to the phospholipid sold under the product name PHOSPHOLIPID PTC by Uniqema (New Castle, Del.), which is further described in U.S. Pat. Nos. 4,503,002 and 4,209,449.

In some embodiments, the glutaurylamidoethyl indole that can be used includes but is not limited to that sold under the product name GLISTIN by Exsymol S.A.M.

In some embodiments, farnesol that can be used is derived from one or more of *Cymbopogon* sp. (Poaceae, citronella), *Citrus aurantium* (Rutaceae, bitter orange), *Cyclamen* sp. (Mursinaceae, *cyclamen*), *Cymbopogon* sp. (Poaceae, lemon grass), *Polianthus tuberose* (Agavaceae, *tuberose*), *Rosa* sp. (Rosaceae, rose), and the like, and combinations thereof.

In some embodiments, the hydrogenated soy lecithin that can be used includes but is not limited to the soy-derived hydrogenated phospholipid sold under the product name LECINOL S-10 by Barnet Products Corporation.

In some embodiments, phytic acid that can be used includes but is not limited to the rice-derived material sold under the product name PHYTIC ACID EXTREME by Biosil Technologies, Inc. (Paterson, N.J.).

In some embodiments, silanediol salicylate that can be used includes but is not limited to the silanol sold under the product name D.S.B.C. by Exsymol S.A.M.

In some embodiments, dimethiconol panthenol that can be used includes but is not limited to that sold under the product name AMINO DL-30 by Biosil Technologies, Inc.

In some embodiments, alpha bisabolol that can be used includes but is not limited to water extracts from chamomile oil, such as the (−)-α-bisabolol sold by Symrise Inc.

In some embodiments, extracts of plants in the Liliaceae family that can be used include but are not limited to aloe extract, such as the aloe barbadensis leaf extract sold by Terry Corporation (Melbourne, Fla.).

In some embodiments, sage extract that can be used includes but is not limited to the extract sold under the product name VEGEBIOS OF SAGE by Barnet.

In some embodiments, rosemary extract that can be used includes but is not limited to the extract sold under the product name VEGEBIOS OF ROSEMARY by Barnet.

In accordance with some embodiments, botanical extracts are used at very low concentrations in compositions that may come in contact with a user's skin (e.g., detergent products and other cleansers). These compositions can be subsequently used for performing tasks such as dishwashing, hand or body washing, and any other action in which detergent/surfactant molecules may come in contact with the skin.

In some embodiments, the at least one botanical extract in the detergent comprises from about 0.0001 to about 10 percent by weight of the detergent. In other embodiments, the at least one botanical extract comprises from about 0.001 to about 5 percent by weight of the detergent. In other embodiments, the at least one botanical extract comprises from about 0.01 to about 3 percent by weight of the detergent. In other embodiments, the at least one botanical extract comprises from about 0.01 to about 1 percent by weight of the detergent.

The nature of the at least one surfactant contained in the detergent is not limited, and includes all manner of potential skin irritants, including but not limited to those described in *McCutcheon's Emuslifiers and Detergents* (McCutcheon's Publications, 2005) *McCutcheon's Functional Materials* (McCutcheon's Publications, 2005), and *Handbook of Industrial Surfactants, Third Edition* (Edited by Michael Ash and Irene Ash, Synapse Information Resources, Inc., 2000). The entire contents of all three documents are incorporated herein by reference, except that in the event of any inconsistent disclosure or definition from the present application, the disclosure or definition herein shall be deemed to prevail. In some embodiments, the surfactants include but are not limited to LAS, SLS, SLES, and combinations thereof. However, embodiments in accordance with the present invention are not limited to detergents containing LAS, SLS, and/or SLES, but may be applicable to any surfactant irritation model.

In some embodiments, methods embodying features of the present invention further include removing at least a portion of the detergent from the skin using water. By way of example, the botanical extract(s) may be provided in a hand dishwashing detergent for washing dishes using water and hand/skin contact. During the dishwashing process, the botanical is allowed to have skin contact and, at low use levels, the cumulative effect is substantial. People washing dishes often subject their hands to such treatments 3 or more times a day for up to 20-30 minutes in warm or hot water.

In some embodiments, the detergent is provided in a "wash off" product, such as a hand dishwashing detergent, liquid hand soap, bar soap, body wash (e.g., adult or baby), shampoos (e.g., adult or baby), hair conditioners, hair rinse, hair colorants, general purpose cleansers, and the like, and combinations thereof. In other embodiments, the detergent is provided in a "leave on" product, such as a skin lotion, skin creme, cosmetic, topical medicament, and the like, and combinations thereof. Notwithstanding, the teachings provided herein are applicable to any skin contact product, including but not limited to "wash off" and "leave on" products.

As described above, a detergent (or more generally any surfactant-containing composition) for use in accordance with the present invention comprises at least one botanical extract, and in some embodiments may include two or more such botanical extracts. Indeed, it has been discovered that in some embodiments, certain combinations of botanical extracts exhibit a surprising and unexpected synergistic enhancement in inflammation reduction (e.g., synergistic suppression of IL-1 alpha secretion). Two such synergistic botanical extracts, further described below, are shiso extract and aloe extract. In some embodiments, the combination of shiso extract and aloe vera gel in a dish detergent system reduced IL-1 alpha secretion by up to about 40%.

In some embodiments, cleansing compositions comprise at least one surfactant, at least one extract of a plant in the Lamiaceae family, and at least one extract of a plant in the Liliaceae family. In some embodiments, the at least one extract of a plant in the Lamiaceae family comprises a shiso extract and the at least one extract of a plant in the Liliaceae family comprises an aloe extract. In some embodiments, the aloe extract comprises aloe vera gel. The shiso extract and the aloe vera gel are present in effective amounts to at least partially counteract skin irritation induced by the at least one surfactant. In some embodiments, the aloe vera gel is not diluted.

Table 2 shows data for the percent reduction in IL-1 alpha secretion in an LAS surfactant base for shiso extract and aloe vera gel when used separately. This liquid dish detergent contained 32% LAS actives, 8% SLES actives, and 5% CDEA actives. As these data show, the highest percent reduction was observed for a composition containing 1% of shiso extract.

TABLE 2

Percent Reduction in IL-1 α Reduction in an LAS Surfactant Base

|  | 1% | 0.10% | 0.01% |
|---|---|---|---|
| Shiso Extract | 13.6 | 11.7 | 1.5 |
| Aloe Vera Gel | 10.4 | 3.0 | −0.4 |

Table 3 shows data for the percent reduction in IL-1 alpha secretion that was observed for a combination of shiso extract and aloe vera gel present in varying amounts in a hand dishwashing detergent. Surprisingly and unexpectedly, the IL-1 alpha reduction observed for these combinations of shiso extract and aloe vera gel was significantly greater than that observed for the individual ingredients. Indeed, the combined presence of shiso extract and aloe vera gel in a hand dishwashing detergent reduced IL-1 alpha secretion by up to about 40%. Moreover, surprisingly and unexpectedly, the best results were observed when shiso extract and aloe vera gel were present in substantially equal concentrations (i.e., a 1:1 ratio by weight).

TABLE 3

Percent Reduction in IL-1 α Reduction for Shiso/Aloe Combinations

| Shiso % | Aloe % | % Improvement |
|---|---|---|
| 0.010 | 0.010 | 40.6 |
| 0.100 | 0.100 | 40.3 |
| 0.100 | 0.010 | 39.6 |
| 1.000 | 0.100 | 39.1 |
| 1.000 | 1.000 | 37.6 |
| 0.010 | 0.100 | 34.3 |
| 0.100 | 1.000 | 33.9 |
| 1.000 | 0.010 | 28.9 |
| 0.010 | 1.000 | 22.2 |
| 0.000 | 0.000 | 0.0 |

As shown in Table 4, a synergistic enhancement is very clearly observed when substantially equal amounts of shiso extract and aloe vera gel are present, with optimum results corresponding to 0.01% concentrations of both the shiso extract and aloe vera gel.

TABLE 4

Percent Reduction in IL-1 α Reduction in Hand Dishwashing Detergent

|  |  | % Aloe | | |
|---|---|---|---|---|
|  |  | 1.000 | 0.100 | 0.010 |
| % Shiso | 0.010 | 22.20 | 34.30 | 40.60 |
|  | 0.100 | 33.90 | 40.30 | 39.60 |
|  | 1.000 | 37.60 | 39.91 | 28.90 |

Accordingly, in some embodiments, the concentrations of shiso extract and aloe vera gel present in a cleansing composition embodying features of the present invention are substantially equal. In some embodiments, these concentrations are between about 0.0001 and about 10 percent by weight of the composition. In other embodiments, the concentrations are between about 0.001 and about 5 percent by weight of the composition. In other embodiments, the concentrations are between about 0.01 and about 1 percent by weight of the composition. In other embodiments, the concentrations are each about 0.01 by weight of the composition.

Table 5 shows data for the percent reduction in IL-1 alpha secretion that was observed for shiso extract and aloe vera gel used separately or in combination in a body shampoo formulation. As these data confirm, the IL-1 alpha reduction observed for the combination of shiso extract and aloe vera gel, both of which were present at a concentration of 0.01%, was significantly greater than that observed for the individual ingredients.

TABLE 5

Percent Reduction in IL-1 α Reduction in Body Shampoo

| 0.01% Shiso Extract | 21.8 |
|---|---|
| 1.0% Aloe Vera Gel | 13.1 |
| 0.01% Shiso Extract & 0.01% Aloe Vera Gel | 27.1 |

The nature of the at least one surfactant contained in a cleansing composition embodying features of the present invention is not limited, and includes all manner of potential skin irritants, including but not limited to LAS, SLS, SLES, and combinations thereof.

Moreover, in addition to shiso extract and aloe vera gel, cleansing composition embodying features of the present invention may further comprise one or more additional botanical extracts, including but not limited to one or more of those described above. It is to be understood that cleansing compositions comprising shiso extract and aloe vera gel may be used in any of the above-described methods of reducing skin irritation, and may be provided in any desired product form, including but not limited to those described above.

The representative formulations described in the following examples illustrate features in accordance with the present invention, and are provided solely by way of illustration. They are not intended to limit the scope of the appended claims or their equivalents.

EXAMPLES

Example 1

Dishwashing Detergent

| Raw Material Description | Supplier | % Final |
|---|---|---|
| Water, Purified or Soft Water |  | 43.641 |
| Primary Alcohol Ethoxylate | Sassol | 3.750 |
| Cocamidopropyl Betaine | McIntyre | 4.026 |
| Cocamide DEA | McIntyre | 16.590 |
| Sodium Pareth - 25 Sulfate (SLES) - Methanol Free | Stepan | 21.402 |
| Adjuvants |  | 10.591 |
|  | Grand Total: | 100.000 |

Example 2

Body Shampoo

| Raw Material Description | Supplier | % Final |
|---|---|---|
| Water, Purified |  | 75.281 |
| Sodium Lauroyl Sarcosinate | Stepan | 2.250 |
| Cocamidopropyl Hydroxysultaine | McIntyre | 1.500 |

-continued

| Raw Material Description | Supplier | % Final |
|---|---|---|
| Sodium Lauryl Sulfate | Stepan | 6.750 |
| Sodium Laureth Sulfate | Cognis | 2.250 |
| Lauramide DEA | McIntyre | 2.250 |
| Adjuvants | | 9.719 |
| | Grand Total: | 100.000 |

The foregoing detailed description and accompanying drawings have been provided by way of explanation and illustration, and are not intended to limit the scope of the appended claims. Many variations in the representative embodiments illustrated herein will be apparent to one of ordinary skill in the art, and remain within the scope of the appended claims and their equivalents.

The invention claimed is:

1. A cleansing composition comprising:
   at least one surfactant;
   from about 0.01 to about 1 percent by weight of the composition of at least one shiso extract; and
   from about 0.01 to about 1 percent by weight of the composition of aloe vera extract;
   wherein the at least one shiso extract and the aloe vera extract are present in a ratio of about 1:1 to counteract skin irritation induced by the at least one surfactant.

2. The composition of claim 1 wherein the at least one shiso extract is present in a range between about 0.01 and about 0.1 percent by weight of the composition and the aloe vera extract is present in a range between about 0.01 and about 0.1 percent by weight of the composition.

3. The composition of claim 1 wherein the at least one shiso extract is present at a concentration of about 0.01 percent by weight of the composition and the aloe vera extract is present at a concentration of about 0.01 percent by weight of the composition.

4. The composition of claim 1 wherein the at least one surfactant is selected from the group consisting of linear alkylbenzene sulfonate ("LAS"), sodium lauryl sulfate ("SLS"), sodium lauryl ether sulfate ("SLES"), and combinations thereof.

5. The composition of claim 1 further comprising at least one botanical extract selected from the group consisting of rosmarinic acid, green tea extract, white tea extract, epicatechin, catechin, epigallocatechin gallate, nasturtium extract, ginko biloba, wheat protein, hydrolyzed lupin protein, Himalayan raspberry extract, oat extract, licorice extract, wheat germ extract, hydrolyzed sesame extract, willowherb extract, grapeseed extract, hydrolyzed linseed extract, algae and mugwort extract, vitamin E, magnesium ascorbyl phosphate, dimethiconol panthenol, vitamin B12, vitamin C, phospholipids, ceramide lipids, glutaurylamidoethyl indole, farnesol, hydrogenated soy lecithin, phytic acid, silanediol salicylate, dimethylsilanol hyaluronate, alpha bisabolol, rosemary extract, sage extract, and combinations thereof.

6. A method of reducing skin irritation induced by a surfactant comprising contacting skin with a detergent comprising at least one surfactant, from about 0.01 to about 1 percent by weight of the composition of at least one shiso extract of a Lamiaceae family plant, and from about 0.01 to about 1 percent by weight of the composition of aloe vera extract, wherein the at least one shiso extract and aloe vera extract are present in a ratio of about 1:1 counteract irritation induced by the at least one surfactant.

7. The method of claim 6 wherein the shiso extract and the aloe vera extract reduce an inflammation response in the skin.

8. The method of claim 6 wherein the shiso extract and the aloe vera extract reduce IL-1 alpha secretion.

9. The method of claim 6 wherein the at least one shiso extract is present in a range between about 0.01 and about 0.1 percent by weight of the detergent and the aloe vera extract is present in a range between about 0.01 and about 0.1 percent by weight of the detergent.

10. The method of claim 6 wherein the at least one shiso extract is present at a concentration of about 0.01 percent by weight of the detergent and the aloe vera extract is present at a concentration of about 0.01 percent by weight of the detergent.

11. The method of claim 6 wherein the at least one surfactant is selected from the group consisting of LAS, SLS, SLES, and combinations thereof.

12. The method of claim 6 wherein the detergent is provided in a wash-off product selected from the group consisting of hand dishwashing detergents, liquid hand soaps, bar soaps, body washes, shampoos, general purpose cleansers, and combinations thereof.

13. The method invention of claim 6 wherein the detergent is provided in a leave-on product selected from the group consisting of skin lotions, skin crèmes, cosmetics, topical medicaments, and combinations thereof.

* * * * *